US00PP16140P3

(12) United States Plant Patent
Garrison et al.

(10) Patent No.: US PP16,140 P3
(45) Date of Patent: Dec. 6, 2005

(54) **ALL-MALE *ASPARAGUS* HYBRID NJ 854**

(50) Latin Name: *Asparagus officinalis*
Varietal Denomination: NJ 854

(75) Inventors: Stephen A. Garrison, Pittsgrove, NJ (US); Chee-kok Chin, Holmdel, NJ (US); John J. Kinelski, Princeton, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 161 days.

(21) Appl. No.: 10/685,344

(22) Filed: Oct. 14, 2003

(65) Prior Publication Data

US 2005/0081270 P1 Apr. 14, 2005

(51) Int. Cl.[7] ..... A01H 5/00

(52) U.S. Cl. ..... Plt./260

(58) Field of Search ..... Plt./260

*Primary Examiner*—Kent Bell
(74) *Attorney, Agent, or Firm*—James A. Lucas; Driggs, Lucas, Brubaker & Hogg Co., LPA

(57) ABSTRACT

A new and distinct all-male *asparagus* (*Asparagus officinalis*) hybrid denoted 'NJ 854' was developed through extensive breeding and selection. *Asparagus* hybrid 'NJ 854' has many desirable traits including vigorous plant growth, high yield, good resistance to rust (*Puccinia asparagi*) and good field tolerance to *asparagus* root rot (*Fusarium oxysporum*) and *asparagus* crown rot (*Fusarium moniliforme*). The plants and plant parts of 'NJ 854' are described as well as the hybrid *asparagus* seeds and plants produced by crossing *asparagus* plant 'NJ 854' with another *asparagus* plant.

1 Drawing Sheet

Latin name of the genus and species: The Latin name is *Asparagus officinalis*.

Variety denomination: The varietal denomination is 'NJ 854'.

BACKGROUND OF THE INVENTION

For an *asparagus* plant to be commercially viable and profitable, good yield is essential. It is well known that *asparagus* is susceptible to a number of diseases. Among the most devastating are rust caused by *Puccinia asparagi* d.c., (Kahn et al. 1952), crown and root rot caused by *Fusarium oxysporum* and crown rot caused by *Fusarium moniliforme* (Johnston et al., 1979; Guerrero et al., 1999). Of course, the presence of these diseases aversely impacts the yields and therefore the profitability of the product. Accordingly, resistance to these diseases is essential.

BRIEF SUMMARY OF THE INVENTION

The invention herein described relates to a new and distinct male *asparagus* hybrid, which we have developed as an elite hybrid with many characteristics desired by growers and consumers. It is distinguished particularly as to its highly desirable traits of vigorous growth habit, high yield, resistance to rust (*Puccinia asparagi*), and good field tolerance to root and crown rot caused by *Fusarium oxysporum* and *Fusarium mondiforme* respectively, as compared to its progenies.

BRIEF SUMMARY OF THE DRAWINGS

Yield of *asparagus* may vary significantly among genotypes. In tests carried out in New Jersey, hybrid 'NJ 854' has produced high yield comparable to Jersey Giant (U.S. Plant Pat. No. 5,551) and Jersey Knight (U.S. Plant Pat. No. 6,624), two of the leading *asparagus* cultivars grown throughout the world. Resistance of rust and tolerance to crown and root rot found in 'NJ 854' will allow growers to plant 'NJ 854' where rust and *Fusarium* now prevent profitable culture of susceptible varieties. The following table shows that in yield the progenies of 'NJ 854' compare very favorably to Jersey Giant and Jersey Knight.

TABLE 1

Figure 1:
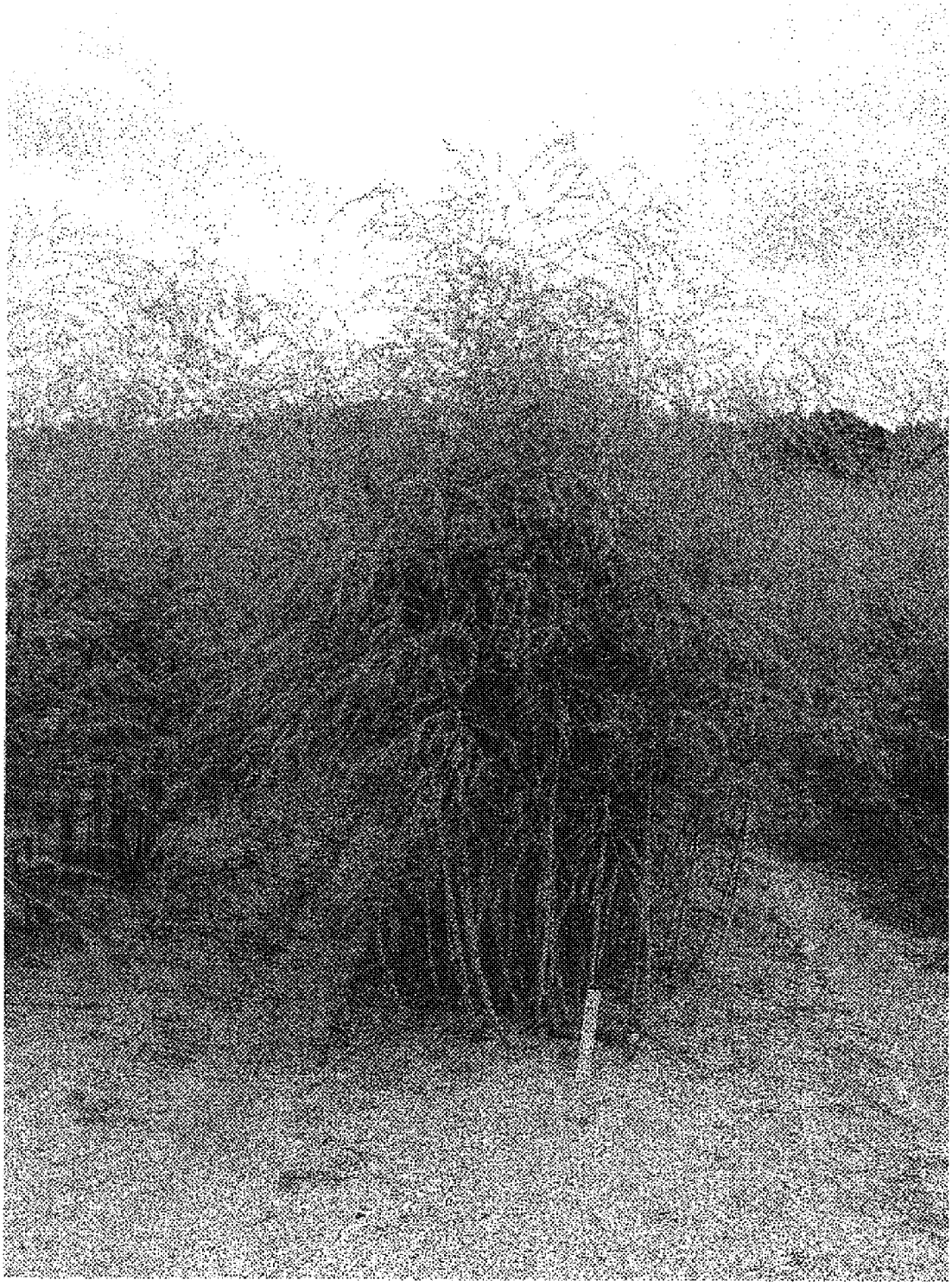

| Crosses | Name | Yield, lb/a |
|---|---|---|
| NJ56 × NJ22-34 | 'NJ854' | 4881 |
| G27 (U.S. Plant Pat. No. 6,168) × NJ22-34 | Not named | 4424 |
| NJ277c (U.S. Plant Pat. No. 6,622) × NJ22-34 | Not named | 4215 |
| G27 × NJ22-8 (U.S. Plant Pat. No. 5,549) | Jersey Gem (U.S. PLANT Pat. No. 6,970) | 3673 |
| NJ362m (U.S. Plant Pat. No. 6,967) × NJ22-34 | Not named | 3645 |
| NJ56 × NJ22-8 | Jersey Giant | 3595 |
| NJ277c × NJ22-8 | Jersey Knight | 3278 |
| NJ362m × NJ22-8 | Jersey General (U.S. PLANT Pat. No. 6,965) | 3155 |

The color notations in our Data Summary have been selected by us from observations as compared with the Munsell Limit Color Cascade. It should be mentioned that foliage color of *asparagus* could be affected by many factors including plant nutrition, temperature, humidity and the density of growth. Furthermore, the coloration is not considered to be a distinguishing feature of this new variety.

FIG. 1 shows in color a typical stalk of a 'NJ 854' *asparagus* plant as it appears in a field under normal conditions.

DETAILED DESCRIPTION OF THE INVENTION

An extensive program of *asparagus* plant improvement, carried out by us in the vicinity of Bridgeton, N.J. and New Brunswick, N.J., has resulted in the development of the asparagus hybrid 'NJ 854' with many desirable traits.

*Asparagus* (*Asparagus officinalis* linn.) is a dioecious species with individual plants being either male or female in sex. In addition to differences in morphology, "cultivars" may also differ in local adaptation, yield, disease resistance, and longevity. Desirable cultivars are developed by the crossing of appropriate elite male and female *asparagus* plants. Both male and female parents transmit traits such as disease resistance, yield, and spear morphology to their progenies. This invention relates to a new and distinct *asparagus* hybrid and its clones designated as 'NJ 854'. Plant 'NJ 854' possesses several desirable traits including vigorous growth habit, higher yield, resistance to rust (*Puccinia asparagi*) good field tolerance to root and crown rot (*Fusarium oxysporum*) and (*Fusarium mondiforme*). 'NJ 854' is produced by crossing female *asparagus* plant 'NJ56' U.S. Plant Pat. No. 5,652 and homozygous male *asparagus* plant 'NJ 22-34' (Unpatented). The *asparagus* hybrid 'NJ 854' is male.

*Asparagus* can be clonally propagated by crown division. The crown is the structure where shoots and roots join together. Division or separation at the crown area will allow the propagation of *asparagus*. We have shown that 'NJ 854' hybrid plants propagated by crown division have similar morphological appearance and possess the same desirable characteristics as the original 'NJ 854' The instant plant reproduces true to type in successive generations of asexual reproduction. Asexual reproduction was carried out at New Brunswick, N.J.

*Asparagus* can also be clonally propagated by tissue culture. An *asparagus* shoot tip or meristem when cultured on appropriate nutrient medium and appropriate conditions can grow, develop, and regenerate into a plant. Also, an *asparagus* plant part such as a spear segment when cultured on appropriate nutrient medium and appropriate conditions can grow, develop, and regenerate into an *asparagus* plant. Such a plant can be efficiently divided and multiplied in appropriate nutrient medium. When propagated by such tissue culture, the 'NJ 854' progeny retains the same desirable characteristics as the original 'NJ 854'.

When crossed with different female plants, *asparagus* 'NJ 854' can transmit many of its desirable traits including vigorous growth habit, higher yield, resistance to rust (*Puccinia asparagi*) good field tolerance to root and crown rot (*Fusarium oxysporum* and *Fusarium mondiforme*) to its progenies.

BOTANICAL DESCRIPTION

Morphological data has been accumulated that distinguishes *asparagus* plant 'NJ 854' from other *asparagus* varieties that has been internally developed, as well as *asparagus* plants that are known and available commercially in the markets.

The data (averages from 3 clones) are assembled from five year old plants located at Rutgers Research and Extension Center in Bridgeton, N.J. The plants are described in the following table:

TABLE 2

| *ASPARAGUS* PLANT: 'NJ 854' |
|---|
| Stalk data: |
| Number of nodes below first branch: 28.3. |
| Distance from crown to first branch: 60.2 cm. |
| Number of branches: 46. |
| Color of ferns on branches: 22-13 |
| Distance between first and last branch: 122.08 cm. |
| Internode length between branches 2.65 cm. |
| Number of cladophyll nodes beyond last branch: 34. |
| Length beyond last branch: 21.25 cm. |
| Largest stalk diameter: 15 mm. |
| Mean diameter of three largest stalks: 14.3 mm. |
| Number of stalks: 29. |
| Highest headed stalk: 45.63 cm. |
| Mature stalks color, bloom removed: Color No. 20-10.5.* |
| Flower data: |
| Typical number per cluster: 2 |
| Tepals - 6 per flower |
| Apex outer surface margin Color No. 26-3.* |
| Apex inner surface margin Color No. 25-3.* |
| Apex outer surface middle (vertical) area Color No. 24-7.* |
| Apex outer surface middle (vertical) area Color No. 26-3.* |
| Base outer surface margin Color No. 24-8* |
| Base inner surface margin Color No. 24-8* |
| Base outer surface middle (vertical) Color No. 19-9* |
| Base outer surface middle (vertical) Color No. 19-8* |
| Shape - elliptic, average 6.2 mm long, 2.6 mm wide at mid-point, slightly wider towards apex, fused in lower third into a tubular corolla, imbricate in bud; apex obtuse; base cuneate; margin entire. |
| Flower length: 6.2 mm. |
| Flower width at midpoint: 2.6 mm. |
| Pedicel: filiform; length - 6 mm; no bract |
| Cladophyll data: |
| Number per node: 5.5. |
| Shape: linear filiform, needle-like; apex acute; base - cuneate; margin - entire; Color - 19-13 throughout |
| Length: 15.05 mm. |
| Width: 0.037 mm. |
| Leaves: |
| Main stem leaves scalelike, triangular, average 12 mm long, 11.5 mm wide at base, membranacous; apex acuminate; base truncate; margin erose, hyaline. Color: 28.11 abaxial; 28-10 adaxial. |
| Terminal branch leaves scalelike, triangular, average 4 mm long, 2 mm wide at base, membranacous; apex acuminate; base truncate; margin erose, hyaline. Color 28.11 abaxial and 28-10 adaxial |
| Reproductive organs: |
| Stamens - 6 in number, each stamen fused to middle of inner side of a tepal |
| Filaments - filiform, straight, slightly wider at base 4.5 mm long; Anthers elliptic, longitudinally dehiscent, introrse to slightly latorose, base sagittate, apex obtuse, with small acuminate tip. |

What is claim is:

1. A new and distinct all-male *asparagus* hybrid plant named 'NJ 854' as herein shown and described.

* * * * *